United States Patent
Payne et al.

(10) Patent No.: US 12,247,054 B2
(45) Date of Patent: *Mar. 11, 2025

(54) CURCUMIN-PEPTIDE CONJUGATES AND FORMULATIONS THEREOF

(71) Applicants: Haus Bioceuticals, Inc., Oklahoma City, OK (US); John Chancey, Edmond, OK (US)

(72) Inventors: Adam J. Payne, Oklahoma City, OK (US); Michael Centola, Oklahoma City, OK (US); John Chancey, Edmond, OK (US)

(73) Assignees: Haus Bioceuticals, Inc.; John Chancey

( * ) Notice: Subject to any disclaimer, the term of this patent is extended or adjusted under 35 U.S.C. 154(b) by 0 days.

This patent is subject to a terminal disclaimer.

(21) Appl. No.: 17/008,912

(22) Filed: Sep. 1, 2020

(65) Prior Publication Data

US 2020/0399331 A1    Dec. 24, 2020

Related U.S. Application Data

(62) Division of application No. 14/710,578, filed on May 12, 2015, now Pat. No. 10,968,260.

(60) Provisional application No. 61/992,123, filed on May 12, 2014.

(51) Int. Cl.
| | |
|---|---|
| *A61K 36/00* | (2006.01) |
| *A61K 31/12* | (2006.01) |
| *A61K 47/54* | (2017.01) |
| *A61K 47/64* | (2017.01) |
| *C07K 14/47* | (2006.01) |
| *C07K 14/76* | (2006.01) |

(52) U.S. Cl.
CPC .............. *C07K 14/47* (2013.01); *A61K 31/12* (2013.01); *A61K 47/542* (2017.08); *A61K 47/64* (2017.08); *C07K 14/4717* (2013.01); *C07K 14/76* (2013.01)

(58) Field of Classification Search
None
See application file for complete search history.

(56) References Cited

FOREIGN PATENT DOCUMENTS

| | | |
|---|---|---|
| WO | 2005025623 A2 | 3/2005 |
| WO | 2011082290 A3 | 11/2011 |
| WO | 2014145851 A1 | 9/2014 |
| WO | 2015092763 A1 | 6/2015 |

OTHER PUBLICATIONS

Amagliani et al. (2017) Trends in Food Science and Technology, 64:1-12. (Year: 2017).*
Tsugita et al. (1994) Electrophoresis 15: 708-720. (Year: 1994).*
Bourassa et al.; "Resveratrol, Genistein, and Curcumin Bind Bovine Serum Albumin"; J. Phys. Chem. B 2010 114:3348-3354.
ConsumerLab.com; "Product Review: Tumeric and Curcumin Supplements and Spices Review," www.consumerlab.com; Apr. 1, 2017, pupated Sep. 14, 2018; pp. 1-44.
Gupta et al.; "Multitargeting by curcumin as revealed by molecular interaction studies"; Nat. Prod. Rep. 2011, 28:1937-1955.
Kanai et al.; "Dose-Escalation and pharmacokinetic study of nanoparticle curcumin, a potential anticancer agent with improved bioavailability, in healthy human volunteers"; Cancer Chemotherapy Pharmacy (2012) 69:65-70.
Li et al., "Binding of cur cumin in B-lactoglobulin and its effect on antioxidant characteristics of cur cumin"; Food Chemistry 141 (2013) 1504-1511.
Li et al., "Whey-protein-stablized nano emulsions as a potential delivery system for water-soluble cur cumin"; LWT—Food Science and Technology 59 (2014) 49-58.
Liu et al.; "On enhancing the solubility of cur cumin by microencapsulation in whey protein isolate via spray drying"; Journal of Food Engineering 169 (2016) 189-195.
Livney; "Milk proteins as vehicles for bioactives"; Current Opinion in Colloid & Interface Science 15 (2010) 73-83.
Sneharani et al.; "Interaction of Curcumin with β-Lactoglobulin-Stability, Spectroscopic Analysis, and Molecular Modeling of the Complex"; J. Agri. Food Chem. 2010, 58, 11130-11139.
Superfoodly; "NovaSOL Curcumin Review: The Patent and 185x Better" Study; www.superfoodly.com; Oct. 26, 2017; pp. 1-50.
Supplementary European Search Report in EP15793294 dated Dec. 1, 2017; pp. 1-9.
Tavares et al., "Milk proteins as encapsulation delivery devices and delivery vehicles: Applications and trends"; Trends in Food Science & Technology 37 (2014) 5-20.
Yi et al., "Glycosylated α-lactalbumin-based noncomplex for curcumin: Physicochemical stability and DPPH-scavenging activity"; Food Hydrocolloids 61 (2016) 369-377.

* cited by examiner

*Primary Examiner* — Russell G Fiebig
(74) *Attorney, Agent, or Firm* — Singleton Law, PLLC; Chainey P. Singleton

(57) ABSTRACT

Disclosed here are compositions comprising a curcuminoid-peptide complex. Also disclosed are methods of preparing a curcuminoid-peptide complex, comprising obtaining a curcuminoid; obtaining a peptide; and mixing the curcuminoid and the peptide in a solvent. Also disclosed are methods of treating a subject, the method comprising identifying a subject in need of treatment of a curcumin-related disorder, and administering to the subject a therapeutic composition comprising a curcuminoid-peptide complex as described. Also disclosed are therapeutic compositions comprising a curcuminoid-peptide complex as described and a pharmaceutically acceptable excipient, diluent, or carrier.

4 Claims, 1 Drawing Sheet

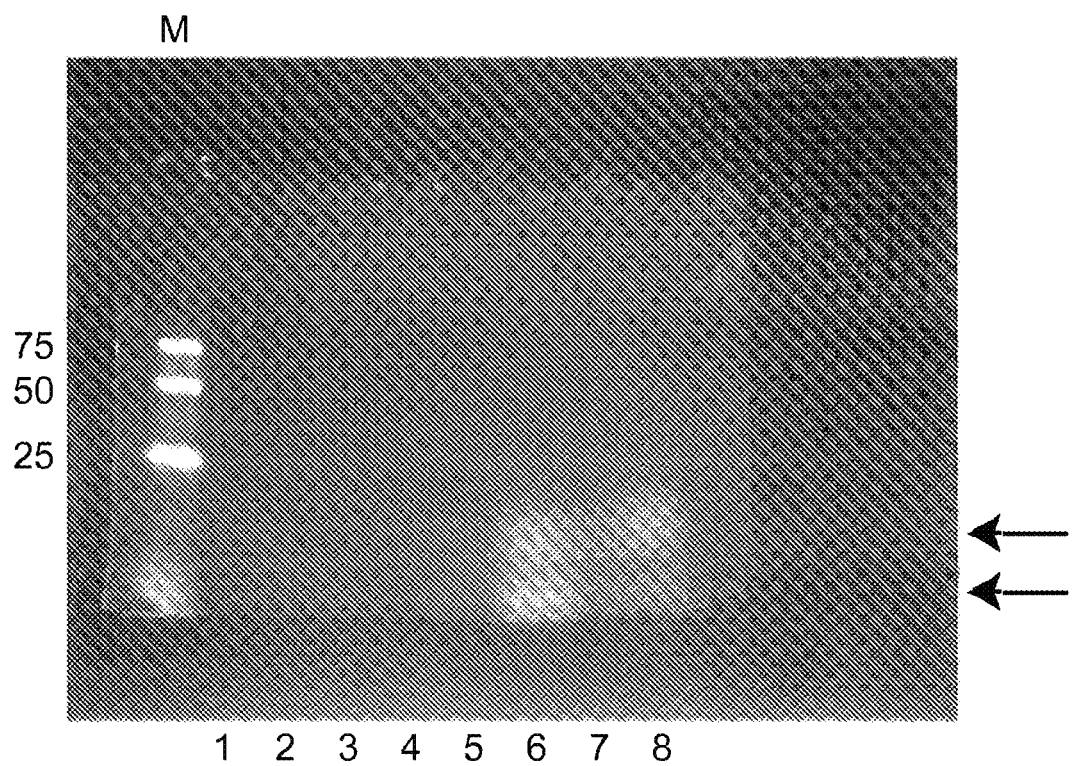

CURCUMIN-PEPTIDE CONJUGATES AND FORMULATIONS THEREOF

RELATED APPLICATIONS

This application is a Divisional Application of co-pending U.S. patent application Ser. No. 14/710,578 filed on May 12, 2015, which claims the benefit of U.S. Provisional Patent Application Ser. No. 61/992,123, filed May 12, 2014, the contents of each are hereby incorporated by reference in their entirety.

FIELD OF THE INVENTION

The present invention is in the field of formulations of nutraceuticals, and more specifically, in the field of formulations having bioavailable curcuminoids.

BACKGROUND OF THE DISCLOSURE

Turmeric is a curry spice obtained from the rhizome of *Curcuma longa* of the ginger family, and has a long history of use in ayurvedic medicine and in traditional Asian diets. The principal bioactive component of turmeric is curcumin (1,7-bis[4-hydroxy-3-methoxyphenyl]-1,6-heptadiene-3,5-dione), a yellow pigment first identified in 1910. Curcumin is used widely in the United States for food coloring (e.g, in mustard, cheese, spices, cereals, potato flakes, soups, pickles, ice cream, and yogurt), and also as a nutraceutical. Recently, Curcumin has become a focus of pharmaceutical development. A June 2011 report stated that 61 clinical trials registered with the U.S. National Institutes of Health were completed or underway on the use of dietary curcumin in treating a variety of clinical disorders.

Commercial curcumin contains curcumin itself (77%), desmethoxycurcumin (DMC, 17%) and bisdesmethoxycurcumin (BDMC, 3%); the latter two differ from curcumin only by lacking one or both methoxy groups, respectively. As a group these compounds and their derivatives for pharmaceutical use are referred to as curcuminoids. Among the major cellular metabolites of these three compounds are the tetrahydrocurcuminoids, in which both vinylidene groups are reduced, i.e., THC (tetrahydrocurcumin), TDMC (tetrahydrodesmethoxycurcumin) and TBDMC (tetrahydrobisdesmethoxycurcumin). The tetrahydrocurcuminoids retain the bioactivity but are colorless and more chemically stable than the curcuminoids.

Curcumin's medicinal properties include reported effects that are antioxidative, anti-inflammatory, antiviral, antibacterial, and antifungal, antiteratogenic, antiproliferative and antimetaststic, and it is safe for human consumption even at the level of 8 g/day ingestion for sustained periods. Studies have shown that to varying degrees curcumin promotes wound healing and has therapeutic and or preventive effects against diabetes, asthma, allergies, cataracts, atherosclerosis, Alzheimer's disease, Parkinson's disease, myelodysplastic syndromes, cystic fibrosis, myocardial infarctions, high cholesterol, stroke, malaria, HIV, HSV-1, psoriasis, and others. Among the diseases for which curcumin has ameliorative effects are autoimmune diseases, including multiple sclerosis, rheumatoid arthritis, psoriasis, inflammatory bowel disease, Sjögren's syndrome, systemic lupus erythematosus, type I diabetes mellitus, neurodegenerative diseases, and several types of cancer.

Medicinal use of curcumin has been limited because the compound is virtually insoluble (dissolution of only ca. 600 ng/mL) in water at acidic and physiological pH and hydrolyzes rapidly at alkaline pH. Plasma concentrations from high human oral doses (8-12 g/day) of curcumin are just in the nanomolar range. Most therapeutic in vitro studies on curcumin have solubilized it in organic solvents. Those solvents include dimethylsulfoxide (DMSO), acetone and ethanol but they have limited suitability for in vivo studies themselves. Curcumin's poor solubility decreases its bioavailability throughout the body, and specifically at the brain, where curcumin does not readily cross the brain-blood barrier.

Consequently, there is an ongoing need for methods and processes that enhance curcumin's bioavailability.

SUMMARY OF THE INVENTION

Disclosed here are compositions comprising a curcuminoid-peptide complex. Also disclosed are methods of preparing a curcuminoid-peptide complex, comprising obtaining a curcuminoid; obtaining a peptide; and mixing the curcuminoid and the peptide in a solvent. Also disclosed are methods of treating a subject, the method comprising identifying a subject in need of treatment of a curcumin-related disorder, and administering to the subject a nutraceutical composition comprising a curcuminoid-peptide complex as described. Also disclosed are therapeutic compositions comprising a curcuminoid-peptide complex as described and a pharmaceutically acceptable excipient, diluent, or carrier.

BRIEF DESCRIPTION OF THE DRAWINGS

FIG. 1 is a photograph of a gel electrophoresis experiment showing curcumin is bound to whey protein.

DETAILED DESCRIPTION OF THE EMBODIMENTS

The present inventors have discovered that the ingestion of a curcumin-peptide complex significantly increases the serum bioavailability of curcumin as compared to the ingestion of uncomplexed curcumin.

Thus, in one aspect, disclosed herein are curcuminoid-peptide complexes comprising a curcuminoid compound linked to a peptide compound.

By "peptide" in the context of a "peptide compound" or a "peptide complex" it is meant a compound composed of one or more amino acids. When the peptide has more than one amino acids, the peptide has at least two amino acids linked together by a peptide bond. In some embodiments, the peptide comprises any of the 20 naturally occurring amino acids, or modified amino acids. In certain embodiments, the compound is an oligopeptide, for example a bipeptide, having two amino acids, a tripeptide, having three amino acids, a 4-mer, 5-mer, and the like. In some embodiments, the oligopeptide comprises between 2-20 amino acids. In other embodiments, the peptide compound is a polypeptide having between 21-100 amino acids. By "N-mer," where N is an integer, it is meant an oligo- or polypeptide having N amino acids.

In other embodiments, the peptide compound is a protein or a protein fragment. In some embodiments, a protein is naturally occurring and is a full sequence polypeptide expressed by a cell. In other embodiments, a protein is a synthetic protein having a sequence that is not found in nature. In some embodiments, the synthetic protein is expressed by a cell using recombinant technologies, whereas in other embodiments, the synthetic protein is synthesized using a peptide synthesizer. A protein fragment is an oligo- or polypeptide having a sequence identical to a sequence fragment found in a protein.

All amino acids, proteins, or peptides within the scope of the present disclosure and claims may be either artificially or naturally occurring or have any forms of modifications (chemical or enzymatic post translational).

In some embodiments, the curcuminoid compound is bound to the peptide compound to form the complex. In these embodiments, the curcuminoid compound is either bound directly to an amino acid of the peptide, or is bound through a linker compound. In some embodiments, the linker is an alkyl, alkenyl, or alkynyl moiety, which may be substituted with a substituent selected from the group consisting of —OH, —SH, —COOH, —N—C(O)H, —N—C(O)OH, —C(O)NH, and the like. In some embodiment, the linker is bound to the amino acid or the curcuminoid compound through a substituent.

In other embodiments, the curcuminoid compound is linked by hydrogen bonding to the peptide compound to form the complex. In yet other embodiments, the curcuminoid compound is linked by electrostatic forces to the peptide compound to form the complex. In yet other embodiments, the curcuminoid compound is linked by lipophilic interactions (e.g., van der Waals forces, or pi stacking) to the peptide compound to form the complex. In other embodiments, the curcuminoid compound is linked by covalent bonding to the peptide compound to form the complex.

In some embodiments, the peptide is a full-length protein. In certain embodiments, the protein is one that is found in the serum of a mammal. In other embodiments, the protein is derived from an animal source other than a mammal. In some of these embodiments, the protein is derived from an avian source, for example an egg protein. In still other embodiment, the protein is derived from plants, such as grains, nuts, legumes, fruits, vegetables, and the like. In some embodiments, the protein is obtained from whey, rice, pea, flaxseed, soy bean, egg. In some embodiments, the protein is albumin. In other embodiments, the peptide comprises cysteine or tyrosine. In certain embodiments, the peptide is N-acetyl cysteine. In certain embodiments, only a single amino acid, for example, cysteine or tyrosine, is used.

In some embodiments, the protein obtained from natural sources is not an isolated and purified protein. Instead, the protein is a mixture of various proteins that are isolated together. These proteins are the isolates of the particular source. Thus, for example, whey protein isolate (WPI) is the mixture of isolated proteins obtained from whey, whereas rice protein isolate (RPI) is the mixture of isolated proteins obtained from rice. Those of ordinary skill in the art know how to obtain protein isolates, for example WPI. Throughout the present disclosure, the terms "whey protein," "whey protein isolate," and "WPI" are used interchangeably.

Examples of oligo- and polypeptides and full-length proteins used in the complexes described herein include, but are not limited to whey protein, tumor necrosis factor (TNF-α); cyclooxygenase (COX) (including COX-1 and COX-2); α1-acid glycoprotein (AGP) (also known as orosomucoid); myeloid differentiation protein 2 (MD-2); any one of the group of enzymes called histone acetyl-transferases (HATs), such as p300/CBP; any one of the group of enzymes called histone deacetylases (HDAC); glyoxalase I (GLOI); xanthine oxidase (XO); a proteasome; sarco (endo) plasmic reticulum $Ca^{2+}$ ATPase (SERCA); human immunodeficiency virus type 1 (HIV-1) protease; any one of the DNA methyltransferases (DNMTs), for example DNMT1; DNA polymerase (pol) λ; any one of the ribonucleases (RNases), for example RNase A; any one of the lipoxygenases (LOXs); any one of the matrix metalloproteinases (MMPs); lysozyme; any one of the protein kinase C (PKC) family of enzymes; cellular sarcoma (c-Src); glycogen synthase kinase (GSK)-3β; ErbB2; phosphorylase kinase; any one of the protein reductases, for example thioredoxin reductase (TrxR) and aldose reductase (ALR2); thioredoxin reductase; any one of the caseins; human serum albumin (HSA); bovine serum albumin (BSA); fibrinogen; β-lactoglobulin (β-LG); α-lactalbumin; human serum immunoglobulin (Ig); FtsZ; transthyretin (TTR); glutathione (GSH); and Kelch-like ECH-associated protein 1 (Keap1).

In some embodiments, the curcuminoid-peptide complex is a complex of curcumin and whey protein isolate (WPI). In certain embodiments, the WPI is a milk-derived whey protein. Milk whey protein is a mixture of β-lactoglobulin (~65%), α-lactalbumin (~25%), bovine serum albumin (~8%), and immunoglobulins. In some of these embodiments, the complex is formed by mixing the curcumin and the WPI in ethanol. Thus, in these embodiments, there is no covalent linkage between the curcumin and the WPI. However, in other embodiments, the curcumin and the WPI form a covalent bond. In certain embodiments, the ratio of curcumin to WPI is 1:1 w/w (mg of curcumin:g of WPI). In other embodiments the ratio of curcumin:WPI is 1:≤10 w/w (mg:g). In still other embodiments the ratio of curcumin:WPI is 10:≥1 w/w (mg:g). In certain embodiments the ratio of curcumin:WPI is 25:1 w/w (mg:g). In other embodiments the ratio of curcumin:WPI is 1:50 w/w (mg:g). In some embodiments, the WPI is obtained from a commercially available source, which comprises 85% WPI in the available powder. In some embodiments, the curcumin is obtained from a commercially available source, which comprises 95% curcumin in the available powder.

In another aspect, disclosed herein is a nutraceutical composition comprising a curcuminoid-peptide complex, as described herein, and a pharmaceutically acceptable carrier, diluent, or excipient.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism. A common carrier is water, where an aqueous solution of the product of interest is prepared and administered to a subject.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In certain embodiments, the same substance can act as a carrier, diluent, or excipient, or have any of the two roles, or have all three roles. Thus, a single additive to the therapeutic composition can have multiple functions.

The term "physiologically acceptable" defines a carrier or diluent that does not abrogate the biological activity and properties of the compound.

The therapeutic compositions disclosed herein may be manufactured in a manner that is itself known, e.g., by means of conventional mixing, dissolving, granulating, dragee-making, levigating, emulsifying, drying, encapsulating, entrapping or tabletting processes.

The therapeutic compositions disclosed herein thus may be formulated in conventional manner using one or more physiologically acceptable carriers comprising excipients and auxiliaries which facilitate processing of the curcuminoid-peptide complex into preparations which can be used nutraceutically. Any of the well-known techniques, carriers, and excipients may be used as suitable and as understood in the art; e.g., in Remington's Pharmaceutical Sciences, above.

For oral administration, the curcuminoid-peptide complex can be formulated readily by combining the curcuminoid-peptide complex with pharmaceutically acceptable carriers well known in the art. Such carriers enable the presently disclosed complexes to be formulated as tablets, pills, dragees, capsules, liquids, gels, syrups, slurries, suspensions and the like, for oral ingestion by a subject. The therapeutic preparations for oral use can be obtained by mixing one or more solid excipient with the disclosed curcuminoid-peptide complexes, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The therapeutic preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

The therapeutic compositions suitable for use in the methods disclosed herein include compositions where the curcuminoid-peptide complex is contained in an amount effective to achieve its intended purpose. More specifically, a therapeutically effective amount means an amount of the curcuminoid-peptide complex effective to prevent, alleviate or ameliorate symptoms of disease or prolong the survival of the subject being treated.

Typically, the dose range of the curcumin administered to the patient is from about 0.5 to 1000 mg/kg of the patient's body weight. The dosage may be a single one or a series of two or more given in the course of one or more days, as is needed by the patient. In some embodiments, the dosages is between 0.1 mg to 50 mg. In other embodiments, the dosage is between 1 mg to 30 mg. Other dose ranges include between 10 to 50 mg, between 20 to 50 mg, between 30 to 50 mg, between 40 to 50 mg, between 20 to 40 mg, between 10 to 20 mg, between 10 to 30 mg, between 20 to 30 mg, and between 30 to 40 mg. The dose may also be at 10 mg, 20 mg, 30 mg, 40 mg, or 50 mg.

In another aspect, disclosed herein is a method of treating a curcumin-related disorder, the method comprising identifying a subject in need thereof and administering to the subject a therapeutically effect amount of a curcuminoid-peptide complex as disclosed herein.

The term "subject" refers to an animal, preferably a mammal, and most preferably a human, who is the object of treatment, observation or experiment. The mammal may be selected from the group consisting of mice, rats, rabbits, guinea pigs, dogs, cats, sheep, goats, cows, primates, such as monkeys, chimpanzees, and apes, and humans.

The term "therapeutically effective amount" is used to indicate an amount of the curcuminoid-peptide complex that elicits the biological or medicinal response indicated. This response may occur in a tissue, system, animal or human that is being sought by a researcher, veterinarian, medical doctor or other clinician, and includes alleviation of the symptoms of the disease being treated.

The term "treat," "treating," "treatment," or any other variation thereof, does not indicate the complete cure from a disorder. Any amelioration of alleviation of the symptoms of a diseases or disorder to any degree, or any increase in the comfort of the subject, is considered treatment.

In another aspect, disclosed herein is a method of treating a curcumin-related disorder, the method comprising identifying a subject in need thereof and administering to the subject a therapeutically effect amount of a curcuminoid-peptide complex as disclosed herein, where subsequent to the administration, the serum $C_{max}$ of curcumin is <500 ng/mL. In some embodiments, the serum $C_{max}$ of curcumin is <0.001% of the administered dose of curcumin.

A "curcumin-related disorder" is a disorder that has been shown to be ameliorated by the administration of curcumin or a curcuminoid compound to the subject. Examples of curcumin-related disorders include, but are not limited to, diabetes, asthma, allergies, cataracts, atherosclerosis, Alzheimer's disease, Parkinson's disease, myelodysplastic syndromes, cystic fibrosis, myocardial infarctions, high cholesterol, stroke, malaria, HIV, HSV-1, psoriasis, and others. Among the diseases for which curcumin has ameliorative effects are autoimmune diseases, including multiple sclerosis, rheumatoid arthritis, psoriasis, inflammatory bowel disease, Sjögren's syndrome, systemic lupus erythematosus, type I diabetes mellitus, neurodegenerative diseases, and several types of cancer.

The definition of the pharmacokinetic parameter $C_{max}$ is well-known to those of skill in the art. Briefly, $C_{max}$ is the maximum observed plasma concentration after a dosage administration.

In another aspect, disclosed herein is a method of preparing a curcuminoid-peptide complex, as described above, the method comprising obtaining a curcuminoid; obtaining a peptide; and mixing the curcuminoid and the peptide in a solvent.

In some embodiments, the solvent is a polar solvent, while in other embodiments, the solvent is an apolar solvent. In some embodiments, the polar solvent is water, whereas in other embodiments, the polar solvent is an alcohol. In some embodiments, the alcohol is ethanol.

In other embodiments, the solvent is an alkaline solution. In these embodiments, curcumin is solubilized in the alkaline solution, and then the protein is added. The solution is then made acidic prior to drying the curcumin-protein mixture.

EXAMPLES

Example 1

Preparation of Curcumin-Whey Protein Isolate Complex

A curcumin-WPI complex was prepared for administration to human subjects. The following materials were used:
WPI: 85% protein by weight
Curcumin powder: 95% curcuminoids
Ethanol: 100% ethyl alcohol
Ratio of curcumin:WPI of 1:50 w/w. A 0.5% w/v tincture (solution) was prepared by mixing 5 g curcumin powder with 1000 mL ethanol. The mixture was placed on a magnetic stirring hot plate, with a speed setting at medium, and temperature setting at 50° C. for 30 minutes or until solution turned clear. To the resulting solution was added 250 g WPI powder. The mixture was placed on a rotary evaporator (rotovap) at slow speed (20-30 rpm), having a water bath temperature of 50° C., and low vacuum for 30 minutes, or until 90% of the ethanol was evaporated. The resulting mixture was placed in a kiln oven to remove the remainder of the ethanol. Alternatively, the mixture was placed in a lyophilizer, or alternatively, was placed in a flow hood or left to air dry.

The curcumin/WPI complex is a fluffy powder with an opaque color in the yellow to orange range. In contrast to pure curcumin, the curcumin:WPI complex powder mixes freely with water, forming a suspension. The curcumin:WPI powder can be easily cleaned from glass, plastic and metal surfaces with detergent. The curcumin:WPI complex only minimally stains clothing. Vigorous washing with detergent solutions is usually sufficient to remove staining.

Ratio of curcumin:WPI of 25:1 w/w (mg:g). The above procedure was repeated, except with 25 mg curcumin powder and 1 g WPI powder. A similar product was obtained.

A standard SDS-PAGE gel of the curcumin:WPI complex was run to determine whether the curcumin was bound to the protein. FIG. 1 shows the resulting gel. This gel was viewed under UV after electrophoresis without fixing or staining. The stain seen in lanes 6-8 is the result of the curcumin staining of the WPI. The lane marked M is the molecular weight marker, which has three fluorescent bands running at 75, 50 and 25 kD. Lane 1-8 correspond to the curcumin:WPI complex at 1, 5, 10, 20, 40, 80, 160 and 320 micrograms of the curcumin:WPI sample, respectively. As can be seen from lanes 6-8, the curcumin is complexed with the WPI. For lanes 1-5, either there is not enough curcumin for visualization or the curcumin is removed by the treatment with SDS-PAGE lysis buffer, heating, or other steps in the procedure.

Example 2

Preparation of Curcumin-Amino Acid Complexes

Following the method of Example 1, curcumin was dissolved in 95% ethanol, followed by the addition of N-acetyl cysteine (NAC). An escalating ratio of the concentrations of curcumin to n-acetyl cysteine was used to find the saturation level. The optimal concentration was found at around 100 mg of curcumin to 1000 mg of NAC in a 0.5% (w/v) solution of curcumin in ethanol. Optimal concentration was noted when low number of Curcumin crystal formation was observed in the macroscopic field.

Similarly, curcumin was dissolved in 95% ethanol, followed by the addition of cysteine. An escalating ratio of the concentrations of curcumin to cysteine was used to find the saturation level. The optimal concentration was found at around 100 mg of curcumin to 1000 mg of cysteine in a 0.5% (w/v) solution of curcumin in ethanol. Optimal concentration was noted when low number of Curcumin crystal formation was observed in the macroscopic field.

Further, a healthy human volunteer subject was dosed with 1.8 grams of the cysteine-curcumin complex. The maximum measured blood concentration of the cysteine-curcumin complex was found to be 300 ng/mL. This compared with two dosing of the 25 mg/g curcumin:WPI complex (equivalent to 50 mg of curcumin), which resulted in a measured blood concentration of 70 ng/mL.

In a similar experiment, curcumin was dissolved in 95% ethanol, followed by the addition of tyrosine. No binding of the curcumin to the tyrosine was observed. The curcumin solidified in a singular layer above the tyrosine layer. When observed under a microscope the tyrosine layer had no visual coloration and the curcumin crystals were completely separate from the tyrosine.

Example 3

Administration of Curcumin:WPI Complex

Two healthy individuals were administered a single dose of the curcumin:WPI complex, having a ratio of curcumin:WPI of 25:1 w/w (mg:g). The dosage contained 25 mg of curcumin. Blood was drawn from each individual at 20 min, 50 min, and 90 min, and the level of serum curcumin was calculated. The results are shown in Table 1, below.

TABLE 1

| Subject A | | | |
| --- | --- | --- | --- |
| Time (min) | 20 | 50 | 90 |
| Avg (ng/mL) | 1426.8 | 1162.0 | 212.7 |
| St Dev | 1200.0 | 932.5 | 51.1 |
| Subject B | | | |
| Time (min) | 30 | 50 | 90 |
| Avg (ng/mL) | 2716.6 | 2011.2 | 508.4 |
| St Dev | N/A | 997.6 | 284.6 |

Example 4

Clinical Studies

A 57 year old male was presented with knee and hip arthritis/bursitis and inflammatory bowel disease. Before dosing he had moderate knee and hip pain and abdominal cramping with moderate diarrhea. Several different dosages and formulations were given. The dosing and the observed effects are summarized in Table 2.

TABLE 2

| Dosage | Effect | Side effects |
|---|---|---|
| 25 mg curcumin bid; (25 mg curcumin/gm WPI) for two weeks | symptom relief from arthritis; less pain with normal & work activities | none noted |
| 1 tsp (10 mg Curcumin/gm WPI) bid in water | +/−skeletal effect; IBD symptom relief | none noted |
| 1 tsp (10 mg Curcumin/gm WPI) tid in water | +/−skeletal effect; IBD symptom relief | none noted |
| 2 tsp (10 mg Curcumin/gm WPI) tid in water | +/−skeletal effect; IBD symptom relief | transient headache |
| 4 tsp (10 mg Curcumin/gm WPI) bid in water | symptom relief from arthritis and IBD | transient headache |
| 4 tsp (10 mg Curcumin/gm WPI) tid in Tang orange drink mix | symptom relief from arthritis and IBD | transient headache; sleep disturbance |
| 4 tsp (10 mg Curcumin/gm WPI) tid in 1 oz plain yogurt | symptom relief from arthritis and IBD | transient headache |
| 35 mg (20% UltraCur in 2 chocolate "buttons") | symptom relief from arthritis and IBD | transient headache |
| 25 mg curcumin bid; (25 mg curcumin/gm Soy Protein isolate) for two weeks | no changes noted | none noted |
| 25 mg curcumin bid; (25 mg curcumin/gm Pea Protein isolate) for two weeks | +/−skeletal effect; IBD symptom relief | none noted |

Example 5

Clinical Studies

Case 1: A 70 year old white female was presented with a history of seasonal depression, which was adequately controlled by Prozac®. The patient was administered 1.2 g of the complex of Example 1 twice a day and experienced complete remission of symptoms after 3 days of use. She continued to take the product to maintain symptom relief and was able to cease the use of Prozac®.

Case 2: A 69 year old white female was presented with a history of mild osteo-arthritis in the hip, lower back and shoulder. The patient was administered 300 mg of the complex of Example 1 three times a day and experienced complete remission of symptoms, including a restoration of range of motion. She ceased the use of NSAID drugs.

Case 3: A 67 year old white male was presented with joint damage and mobility impairment as a secondary result of childhood polio infection. The patient was administered 1.2 g of the complex of Example 1 twice a day for two weeks for complete remission of symptoms. He continued to take the product to maintain symptom relief.

Case 4: A 65 year old white male was presented with mobility impairment from multiple traumatic injuries sustained over 20+ years. The patient was administered 1.2 g of the complex of Example 1 twice a day for two weeks and reported 50% improvement in symptom relief.

Case 5: A 47 year old white male was presented with a history of tennis elbow refractory to all NSAID treatment. He was unable to apply any weight to his affected arm. He reported complete remission of symptoms after taking an equivalent dose of 1.5-2.0 g of the complex of Example 1 twice a day for two weeks mixed in TANG. He continues to take the product to maintain symptom relief.

Case 6: A 28 year old white male was presented with a history of seasonal allergies. The patient was administered 1.2 g of the complex of Example 1 twice a day for two weeks for complete remission of seasonal allergy symptoms. He continued to use product to maintain symptom relief.

Case 7: A 47 year old white male was presented with reporting pain and loss of mobility from an ankle break that occurred 1 year ago. The patient reported complete symptom relief and recovery of mobility with use of 1.2 g of the product of Example 1 twice a day for two weeks. He continues to take product to maintain symptom relief.

Case 8: A 50 year old white female was presented with a history of manic depression. The patient was administered 1.2 g of the complex of Example 1 twice a day for two weeks with moderate relief of symptoms of depression and reported clearer thinking and mood elevation.

Case 9: A 67 year old white male was presented with a history of mild arthritis in right shoulder. The patient was administered 1.2 g of the complex of Example 1 twice a day for two weeks with significant relief of arthritis symptoms.

Case 10: A 75 year old female was presented with debilitating arthritis in both ankles. She had pain at rest, and was ambulatory primarily in a wheelchair, with minimal ability to stand or walk with a walker. She used various NSAIDs and prescription anti-pain narcotics daily. The patient was administered 25 mg curcumin three times a day (25 mg curcumin/g WPI) for two weeks. She obtained symptom relief from arthritis, which included decreased pain and increased mobility without the use of a wheelchair or a walker. She discontinued the use of the narcotics and NSAIDs.

Case 10: A 60 year old female was presented with arthritis in hand with pain at rest and increased pain during work activities (rural farm work). She used various NSAIDs daily. The patient was administered 25 mg curcumin bid; (25 mg curcumin/g WPI) for two weeks. She obtained symptom relief from arthritis and was able to increase work activities. She discontinued the use of NSAIDs. After three months of curcumin treatment, she discontinued the use of the curcumin product for 3 weeks and repeated the bid dose of curcumin with the same results.

Case 11: A 61 year old male was presented with severe hip osteo-arthritis/bursitis, exhibiting pain at rest, decreased mobility, and increased pain during work activities (rural farm work). The patient was using various NSAIDs daily and was scheduled for a hip replacement surgery. The patient was administered 25 mg curcumin bid (25 mg curcumin/g WPI) for two weeks. He experienced symptom relief from arthritis, which included increased mobility and increased ability to perform work activities easier and with less pain.

Case 12: A 50 year old female was presented with arthritis in shoulders, hips and knees, and pain in feet. The patient exhibited pain at rest and decreased mobility, such that the patient required the assistance of a walking cane. The patient was administered 25 mg curcumin bid (25 mg curcumin/g WPI) for two weeks. She displayed symptom relief from arthritis, along with increased mobility with less pain.

Case 13: A 55 year old female was presented with arthritis in knees, along with knee pain with daily and work activities. The patient was administered 12.5 mg curcumin bid (1 gram curcumin:WPI product) for two weeks. She displayed symptom relief from arthritis, along with less pain with daily and work activities.

Case 14: A 45 year old female was presented with knee and shoulder arthritis. The knee and shoulder pain was pronounced with normal and work activities (rural farm work). The patient was administered 12.5 mg curcumin bid (1 gram curcumin:WPI product) for two weeks. She displayed symptom relief from arthritis, along with less pain with daily and work activities.

Case 15: A 60 year old male was presented with arthritis in knees, along with knee pain with normal and work activities (rural farm work). The patient was administered 25 mg curcumin bid (1 gram curcumin:WPI product) for two weeks. He displayed symptom relief from arthritis, along with less pain with daily and work activities.

Case 16: A 60 year old male was presented with lymphoma and multi-focal enlarged lymph nodes. The patient was administered 25 mg curcumin bid (25 mg curcumin/g WPI) for two weeks. He displayed moderate shrinking of affected lymph nodes after two weeks. Further use of material did not have any further effect.

Case 17: A 57 year old male was presented with arthritis in knees, bursitis in hips, and moderate knee and hip pain with normal and work activities. The patient was administered 25 mg curcumin bid (25 mg curcumin/g WPI) for two weeks. He displayed symptom relief from arthritis, along with less pain with daily and work activities.

Case 18: A 57 year old male was presented with inflammatory bowel disease, along with attendant abdominal cramping, and mild to moderate diarrhea. The patient was administered 25 mg curcumin bid (25 mg curcumin/g WPI) for two weeks. He displayed symptom relief from IBD, along with complete relief from abdominal cramping; firm stools.

Case 19: A 58 year old male was presented with knee and back pain associated with normal and work activities. The patient was administered 25 mg curcumin bid (25 mg curcumin/g WPI) for two weeks. He displayed symptom relief from arthritis, along with less pain with daily and work activities.

Case 20: A 67 year old female was presented with advanced Alzheimer's disease. Prior to dosing, she failed all short term memory questions on a test. The patient was administered 1.2 g curcumin bid. After 30 days, she passed all short term memory questions on the test. She has continued to have lasting benefit from the therapy.

Example 6

Animal Studies

Case 1: An 11 year old QH gelding horse was presented with osteo-arthritis in both right and left front ankles. It showed pain on flexion of ankles and "rough gait" at gallop. It was orally administered 200 mg of the product of Example 1 twice a day. After one week, the horse showed decrease pain on flexion of ankles and smooth gait at gallop, along with calming or decrease anxiety. There was no adverse side effect.

Case 2: A 5 year old spayed female dog was presented with osteo-arthritis. It showed pain on flexion of front limbs and decreased mobility. It was orally administered 25 mg of the product of Example 1 twice a day. After one week, the dog showed decreased pain on limb flexion, increased mobility, increased running, and increased appetite. There was no adverse side effect.

Case 3: An 11 year old QH gelding horse was presented with pain on flexion of front ankles and decreased mobility. It was administered 800 mg of the product of Example 1 via naso-gastric tube one time. After 4 hours, the horse showed decrease pain on flexion of ankles, along with pronounced calming and sedative affects. There was no adverse side effect.

Case 4: A 2 year old QH filly was presented as anxious and apprehensive. It was very nervous in the race training environment and was stalled with limited interaction with other horses. It also showed decreased appetite. It was orally administered 200 mg of the product of Example 1 twice a day. After one week, the horse showed decreased anxiety and nervousness in stall, with a concomitant increased appetite. There was no adverse side effect.

Example 7

Bioavailability of the Curcumin:WPI Complex

Curcumin:WPI complex: Six mice were each dosed with 12.5 mg of the curcumin:WPI complex (~312 μg of curcumin per mouse). Mice weighed ~25 g each. Blood was drawn every 30 minutes for 180 total minutes. Average values of curcumin (in ng/mL) are shown in Table 3. Average Tmax was 60 minutes and average Cmax was 163 ng/mL of curcumin.

TABLE 3

| | | Curcumin: WPI complex | | | | | |
|---|---|---|---|---|---|---|---|
| Time (Mins) | Avg (ng/mL) | 1 | 2 | 3 | 4 | 5 | 6 |
| 30 | 27 | 45 | 58 | 12 | BDL | 10 | 10 |
| 60 | 163 | 201 | 656 | 38 | 32 | 38 | 13 |
| 90 | 49 | 20 | 109 | 12 | 77 | 23 | 53 |
| 120 | 94 | 127 | 34 | BDL | BDL | 204 | 11 |
| 150 | 27 | 40 | 13 | BDL | BDL | BDL | BDL |
| 180 | BDL | BDL | BDL | BDL | BDL | BDL | BDL |

BDL = Below Detectable Limit (10 ng/mL)

Curcumin: Six mice were each dosed with 0.625 mg of curcumin (about twice the amount of curcumin as administered as a complex, above). Mice weighed ~25 g each. Blood was drawn every 30 minutes for 180 total minutes. Average values of curcumin (in ng/mL) are shown in Table 4 below.

TABLE 4

Curcumin

| Time (Mins) | 1 | 2 | 3 | 4 | 5 | 6 |
|---|---|---|---|---|---|---|
| 30 | BDL | BDL | 21 | BDL | BDL | BDL |
| 60 | BDL | BDL | BDL | BDL | BDL | BDL |
| 90 | BDL | BDL | BDL | 136 | BDL | BDL |
| 120 | BDL | BDL | BDL | BDL | BDL | BDL |
| 150 | BDL | 22 | BDL | BDL | BDL | BDL |
| 180 | BDL | BDL | BDL | BDL | BDL | BDL |

BDL = Below Detectable Limit (10 ng/mL)

As the data shows, free curcumin has very poor absorbability, such that its plasma concentrations are invariably below the detectable limit. However, when curcumin is complexed with whey protein isolate (WPI), it becomes readily bioavailable.

Example 8

Pharmacokinetics of the Curcumin:WPI Complex

Two healthy volunteers were administered various formulations of curcumin at several different doses. Blood was obtained by the finger stick method from each individual at various time points. The plasma concentration of curcumin was calculated and the $C_{max}$ was determined. The results are shown in Table 5

TABLE 5

| | Subject 1 | | Subject 2 | |
|---|---|---|---|---|
| Dosage | Cmax ng/mL | Formulation | Cmax ng/mL | Formulation |
| 16.5 mg | nd | Curcumin/WPI (10 mg/g) | nd | Curcumin/WPI (10 mg/g) |
| 2000 mg | 15 | Curcumin C3 complex w/10 mg Bioperine | N/A | N/A |
| 25 mg | 2122 | Curcumin/WPI (25 mg/g) | 1114 | Curcumin/WPI (25 mg/g) |
| 30 mg | ~3,000 | Curcumin/WPI (10 mg/g) | ~1,500 | Curcumin/WPI (10 mg/g) |
| 36 mg | 500 | Curcumin/BiPro WPI (20 mg/g) | N/A | N/A |
| 36 mg | 900 | Curcumin/WPI (20 mg/g) | N/A | N/A |
| 38 mg | N/A | N/A | 34 | Curcumin/WPI (25 mg/g) |
| 45 mg | 600 | Curcumin/WPI (25 mg/g) | N/A | N/A |
| 48 mg | 70 | Curcumin/WPI (25 mg/g) mixed in dark chocolate@ 20% | N/A | N/A |
| 50 mg | 75 | Curcumin/RPI (25 mg/g) | N/A | N/A |
| 50 mg | 70 | Curcumin/WPI (25 mg/g) | N/A | N/A |
| 50 mg | nd | Curcumin/WPI (25 mg/g) | N/A | N/A |
| 55 mg | 16 | Curcumin/WPI (25 mg/g) | N/A | N/A | nd = Not detected
N/A = Not available; data was not obtained

What is claimed is:

1. A composition comprising a curcumin conjugated to a rice protein to form a curcuminoid-rice protein complex with a curcumin to rice protein ratio of is 1:1 (mg:g), or 1:≤10 (mg:g), or 10:≥1 (mg:g), or 25:1 (mg:g), or 1:50 (mg:g).

2. The composition of claim 1, wherein the curcuminoid is selected from the group consisting of curcumin, desmethoxycurcumin (DMC), bisdesmethoxycurcumin (BDMC), tetrahydrocurcumin (THC), tetrahydrodesmethoxycurcumin (TDMC), tetrahydrobisdesmethoxycurcumin and (TBDMC).

3. The composition of claim 1, wherein the curcuminoid and the rice protein are conjugated by a covalent bond, an ionic interaction, a lipophilic (van der Waals) interaction, or a hydrogen bond.

4. The composition of claim 1, wherein the curcuminoid-rice protein complex is obtained by process of mixing the curcuminoid and the rice protein in a solvent.

* * * * *